United States Patent [19]

Lechner et al.

[11] 3,978,686

[45] Sept. 7, 1976

[54] PROCESS FOR TRANSFERRING AND/OR HANDLING OF A COLD TISSUE SECTION ESPECIALLY OBTAINED FROM AN ULTRAMICROTOME AND ARRANGEMENTS FOR PRACTICE OF THE PROCESS

[75] Inventors: Günther Lechner; Ferdinand Pauliny, both of Vienna, Austria

[73] Assignee: C. Reichert Optische Werke AG, Vienna, Austria

[22] Filed: Mar. 31, 1975

[21] Appl. No.: 565,988

[30] Foreign Application Priority Data

Mar. 29, 1974 Austria .................. 2653/74

[52] U.S. Cl. .................. 62/514 R; 62/DIG. 1
[51] Int. Cl.² .................. F25B 19/00
[58] Field of Search .......... 62/514 R, 172, DIG. 1, 62/DIG. 9

[56] References Cited
UNITED STATES PATENTS

| | | | |
|---|---|---|---|
| 3,066,222 | 11/1962 | Poorman et al. | 62/514 R |
| 3,296,825 | 1/1967 | Kanzig | 62/514 R |
| 3,327,491 | 6/1967 | Andonian | 62/514 R |
| 3,332,254 | 7/1967 | Elovic et al. | 62/514 R |
| 3,398,549 | 8/1968 | Zobel | 62/514 R |

*Primary Examiner*—Lloyd L. King
*Attorney, Agent, or Firm*—Alan H. Spencer; William C. Nealon; Howard R. Berkenstock, Jr.

[57] ABSTRACT

A method and apparatus for transferring frozen sections from a microtome or ultramicrotome to a microscope or the like without the deleterious effects of the ambient conditions. The apparatus includes a temperature regulated cooling means and protective enclosure to protect the frozen specimen during the transfer. The apparatus can be plugged into the vacuum chamber of an electron microscope and then the protective enclosure removed to present the frozen specimen for examination.

6 Claims, 5 Drawing Figures

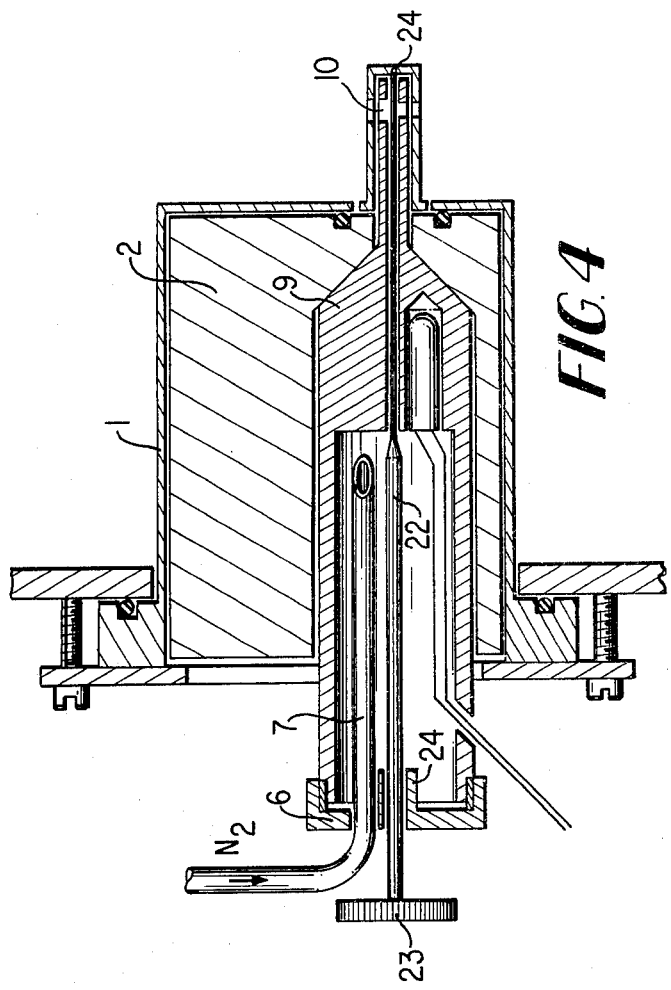
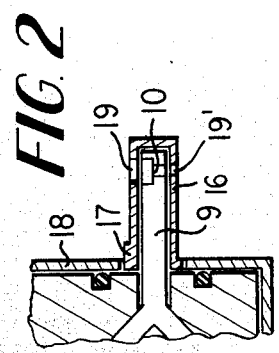
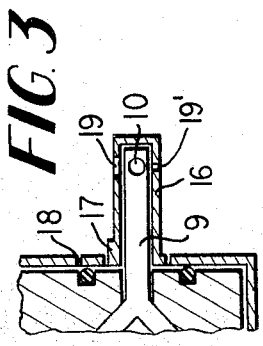
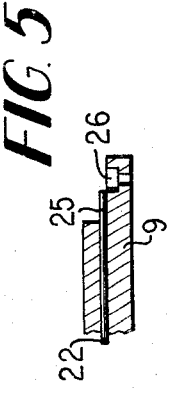

PROCESS FOR TRANSFERRING AND/OR HANDLING OF A COLD TISSUE SECTION ESPECIALLY OBTAINED FROM AN ULTRAMICROTOME AND ARRANGEMENTS FOR PRACTICE OF THE PROCESS

BACKGROUND OF THE INVENTION

In the production of ultra-thin biological specimen sections, especially for examination under a microscope an electron microscope, freezing of the specimen from which these sections are produced is frequently necessary. This is especially true with biological specimens having a high water content. It is of prime importance to be able to further maintain the frozen sections at very low temperatures, without any significant increase in temperature even for a short time. Also, care must be taken to prevent water condensing (or subliming) on the frozen section, since this would affect water-soluble components in the section and surface structure. Maintenance of the dry frozen condition must be uninterrupted right up to the final treatment or observation and frequently it must be continued during such a treatment or observation, for example, to prevent vaporization of substances contained in the specimen to be examined. Heating, which in the course of observations with an electron microscope can be caused by the electron beam and, at temperatures in the range of −70° to −80°C. would cause in recrystallization, making the specimen useless. In this connection, it should be mentioned that observation by an electron microscope requires the specimen to be located in an evacuated chamber enabling partial sublimation to occur at temperatures in the order of −90°C. These difficulties are known, but the known methods and devices only partially overcome these problems and are also restricted to a few special uses.

Thus, ultramicrotomes with a freezing attachment are known and used to produce frozen sections. It is also known to use a carrier (which in itself is not frozen) for the transporting of a specimen to an electron microscope. Such carriers are pre-cooled to a low temperature but, in spite of the short time required for conveyance, the specimen is not adequately protected. Another uses a liquid-nitrogen filled, container as a carrier and the specimen floats on the liquid nitrogen as in an ultramicrotome.

It is also known that the stage of an electron microscope may be precooled and to use a specimen holder which forms part of the object stage as a transfer device. A device is known for transferring a frozen specimen located in a container of liquid nitrogen, in a dry nitrogen atmosphere, to the lock chamber of an electron microscope having a precooled stage. This device results in a brief by significant period of an elevated temperature having a deleterious effect on the specimen. Even this device does not solve the problems of removing and preserving a biological specimen section produced in the freezing chamber of an ultramicrotome in a dry, frozen state or the task of maintaining the specimen at a predetermined cryogenic temperature during further manipulations. Such devices do not prevent exposure for a short time to the ambient atmosphere during removal from the ultramicrotome.

It is an object of the present invention to provide a device capable of maintaining a biological section in a stable cryogenic environment during transfer from a sectioning instrument such as an ultramicrotome, or to a treatment or observation device.

It is another object of the present invention to provide an uncomplex, low cost device for transferring a section removed from the freezing chamber of an ultramicrotome inserting the device into the freezing chamber.

A further object of the present invention is a device which is self-cooled and temperature-regulated.

A still further object of the present invention is a vacuum chamber enabling the chamber and transfer device to form a separable unit, so that the transfer device therefore, with the section, can be conveyed without difficulty from one treatment or observation instrument to another, and coupled thereto. This is especially significant, if an intermediate treatment of the specimen section is to be conducted, as for instance etching, during which it must be possible to vary the temperature of the section.

It has been found that it is unnecessary to protect the specimen from water condensation by transfer in vacuum which has been frequently done. Rather it is sufficient to convey the section in a small convered recess in which is inserted inside of the freezing chamber of an ultramicrotome, having an inert, dry, cold gas atmosphere to receive the specimen.

THE PRESENT INVENTION

A BRIEF DESCRIPTION

The present invention relates to a method for the transferring and/or treatment of a frozen biological section, especially of ultramicrotome sections, and devices for the implementation of the method. The method according to the invention is characterized by the fact that the section is first placed in a cooled enclosure of transfer device without removal from the freezing chamber where it was produced. The enclosure is then covered and the transfer device together with the section removed from the cooling chamber. The specimen is thus under continuous, preferably temperature-regulated, freezing conditions in the treatment device and during transfer to an electron-scanning microscope or the like. The transferring device is connected to the microscope by an air lock and the cover removed from the enclosure to present the specimen for examination. The transfer device according to the invention is equipped with a self-cooling system using liquid gas, as for instance nitrogen and is preferably regulatable. The device may have means fitting air locks which are provided in the vacuum chambers of treatment devices, electron microscopes and the like.

FIG. 2 shows in longitudinal section the finger of a transferring device in the open position;

Figure 1:
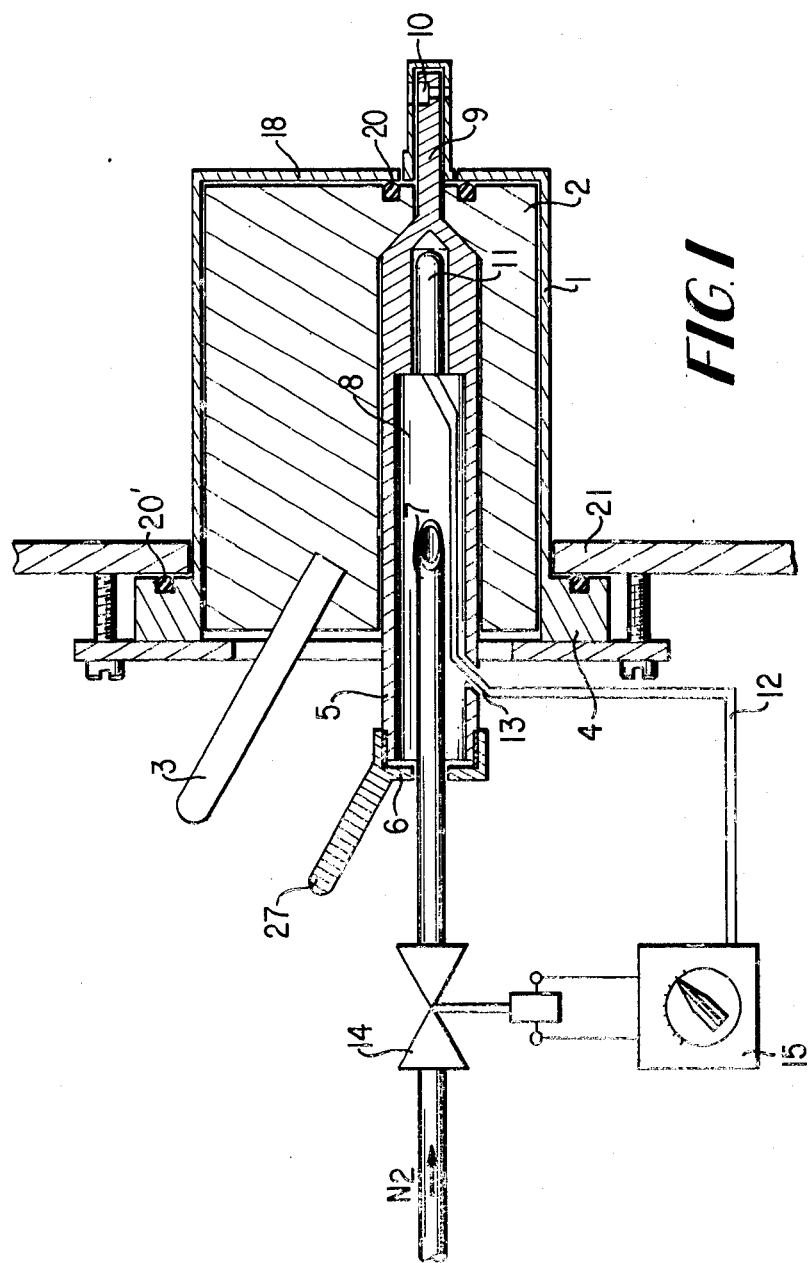
FIG. 1 shows in longitudinal section a transfer device, which is positioned in an air lock.

FIG. 3 finger in the closed position;

FIG. 4 shows in section another embodiment; and

FIG. 5 shows in longitudinal section the finger of the embodiment of FIG. 4.

DESCRIPTION OF THE PREFERRED EMBODIMENT

FIG. 1 shows a cylindrical air lock of conventional structure, which comprises a metallic outer casing 1 with a flange 4 and the transfer device located therein. A thermally insulating cylinder 2 together with the grip 3 jackets the transfer device. Transferring device has Cylinder 5 of the device has an expansion chamber 8 into which liquid nitrogen flows. The prolongation of the chamber 8, which is fed with coolant from tube 7 has a small recess in which temperature gauge 11 is located. Temperature gauge 11 may be thermal resistor with a temperature function, linked by electrical leads 12 to nitrogen regulator 15. Regulator 15 is preferably adjustable, so that different temperatures cam be selected and maintained. Regulator 15 controls electrically valve 14, which located in the line feeding liquid nitrogen to the transferring device. The escape of excess coolant from chamber 8 of the transferring device takes place through outlet 13, through which the electrical leads 12 may be also conducted. The transfer device body 8 has its outer surfaces constructed to fit into the synthetic cylinder 2 to provide a satisfactory vacuum seal. Finger 9 possesses a passage 10 for receiving and supporting the specimen section with shield 16. Finger 9 has heat removed by conduction through body 5 and the section (not shown) in passage 10 is protected from external heat by shield 16. Also, venting may be conducted through cover 6. It is essential, however, that tube 7 extend as far forward as possible into the area of the tapering of the body 5, in order to achieve the best effective cooling of finger 9 with the specimen. Jacket 2 is manually rotatable by grip 3 relative to casing 1 of the air lock which has front wall 18 with an aperture, through which finger 9 extends into the vacuum chamber not shown. On the front side of the synthetic (plastic), a ring-shaped gasket 20 provides a seal between jacket 2 and air lock wall 18. A similar packing 20' likewise seals flange 4, against the outer wall 21 of the vacuum chamber.

The purpose of the rotating body 5 can be seen from FIGS. 2 and 3. In these figures, an advantageous construction of shield 16 of the specimen-receiving recess is exemplified. Shield 16 protects substantially all of finger 9 that extends beyond jacket 2 and has on its rear end a lug 17. Loosening the locks permits rotation of jacket 2 for alignment of lug 17. Lug 17 engages a conventional radial recess, designed to prevent concurrent rotation of shield 16 and finger 9. Apertures 19 and 19¹ are provided in the shield 16, and are located to selectively expose passage 10 for placing a section therein or examination of the specimen. FIG. 2 shows passage 10 exposed by alignment or apertures 19 and 19¹ therewith. FIG. 3 shows passage 10 closed and in this position, the transfer device together with the specimen, can then be removed from the microtome or vacuum chamber without heat affecting the specimen. After the introduction of the transfer device into a vacuum chamber, whicn pertains to another treatment or observational device, passage 10 is exposed by rotation of the handle 27. Naturally, the shield 16 is connected to the finger 9 to prevent longitudinal displacement, as for instance by means of a ring-type groove (not shown) located in finger 9, and a projection (not shown) on the inner side of shield 16 engaging said groove. On introducing the transfer device into the air lock care must only be taken so that the lug 17 engages in the recess of the front wall 18, that is, insert the transfer device in the correct location. In order to determine this location, a stop or pointer can be provided on flange 4 and on the jacket 2.

FIG. 5 shows another arrangement of a self-cooled transfer device with a shielded passage. Passage 10 can be opened and closed from the rear of the transfer device by means of a rod 22 extending through the center of body 5 and finger 9, respectively, with a handle 23 at one end and attached to shield 24 at the distal end. Shield 24 is rotatably connected to finger 9 and selectively covers the passage 10 when in the position illustrated by the drawing. If the rod 22, journaled in cap 6, is rotated by knob 23 until lug 17 engages a stop on wall 18, then shield 24 is likewise rotated and exposes passage 10, in which the section is located.

A further exemplification is shown by FIG. 5, where rod 22 has a flattened end 25. This end 25 acts as the shield, which can be slid over the aperture 10. In connection therewith, the distal end of the finger 9 is constructed so that flat surface 26 mates with covering 25. The rod 22 may have a slit or a hole, which exposes aperture 10 is retracted sufficiently to effect such exposure.

Likewise, different forms can be conceived of the remaining portion of the transfer device. Thus for instance, instead of a single cavity fed with a fluid, several chambers could be used and even could be connected together. Plural Chambers would enable switching to an appreciably changed temperature, for instance, the coolant could be removed or a fluid of a very different temperature could be introduced into another chamber. In order to avoid solidification of some heating fluids, they may have to be forced through under a high pressure at great speed.

It is also possible to provide an electric resistance in the transfer device near its front end, instead of a fluid heating. However, the temperature sensor would have to be placed even further forward, that is, nearer the passage for the receiving of the specimen section. The heating resistor could be connected with a control to regulate performance. It could also be briefly overloaded, in order to obtain a rapid temperature change.

It is advantageous to construct the transfer device as a unit with the slightest possible heat capacity, and to insulate it in the best possible manner against heat absorbtion or loss. For this purpose, the thinnest possible wall construction having least possible heat capacity should be utilized, such as aluminum which has good heat conductivity. The finger extending from the larger cylinder of the transfer device, can be made out of two different materials, so that the inner portion serves as a heat conductor and the outer as a heat insulator. For instance, the finger could be of two concentric parts providing a heat capacity of the transfer device at the distal end that is reduced to a minimum, and a thermal inertia diminished to a minimum possible volume, so that a rapid temperature control is achieved.

What is claimed is:

1. Apparatus for transferring a frozen section from a microtome without an increase in temperature deleterious to the section which comprises, a body having an expansion chamber, a source of compressed fluid operably connected to said expansion chamber to cool said body, a heat conductive finger extending from said body, said finger having a transverse passage adjacent its distal end, said passage having a support to receive said frozen section, a shield adapted to selectively cover and provide access to said passage for placing the frozen section therein and permitting examination of said frozen section, whereby expansion or fluid in said chamber removes heat from said finger to prevent warming of the section during the transfer.

2. The apparatus according to claim 1 wherein said body is elongated and further including a jacket of heat insulating material to reduce the transfer of heat to said body.

3. The apparatus according to claim 1 wherein said body is cylindrical and said finger extends from an end thereof.

4. The apparatus according to claim 3 further including a jacket of heat insulating material and wherein said body is manually rotatable relative to and within said jacket and said shield.

5. The apparatus according to claim 1 further including means to regulate flow of the compressed fluid to said expansion chamber.

6. The apparatus according to claim 5 further including temperature sensitive means located in said body to control said means to regulate flow of the compressed gas.

* * * * *